(12) United States Patent
Reno et al.

(10) Patent No.: US 6,483,418 B1
(45) Date of Patent: Nov. 19, 2002

(54) CREEP ACTING MINIATURE THERMOSTATIC ELECTRICAL SWITCH AND THERMOSTATIC MEMBER USED THEREWITH

(75) Inventors: Debra E. Reno, Franklin, MA (US); Brian J. Simoes, N. Dighton, MA (US); George R. Holman, Attleboro, MA (US)

(73) Assignee: Texas Instruments Incorporated, Dallas, TX (US)

( * ) Notice: Subject to any disclaimer, the term of this patent is extended or adjusted under 35 U.S.C. 154(b) by 73 days.

(21) Appl. No.: 09/641,324

(22) Filed: Aug. 18, 2000

(51) Int. Cl.[7] .................... H01H 37/52; H01H 37/54
(52) U.S. Cl. .................. 337/379; 337/362; 337/380; 337/111
(58) Field of Search .................. 337/362, 36, 111, 337/1, 112, 113, 343, 372, 373, 342, 365, 379, 380; 29/622

(56) References Cited

U.S. PATENT DOCUMENTS

| 3,430,177 | A |   | 2/1969  | Audette |
|-----------|---|---|---------|---------|
| 3,648,273 | A | * | 3/1972  | Gardner ........................ 337/88 |
| 3,670,280 | A | * | 6/1972  | Nagele ......................... 337/111 |
| 3,818,403 | A | * | 6/1974  | Ambler ........................ 337/109 |
| 4,319,214 | A | * | 3/1982  | Givler ......................... 337/343 |
| 4,389,630 | A | * | 6/1983  | Ubukata et al. ............. 337/363 |
| 4,647,893 | A | * | 3/1987  | Sindlinger ................... 315/104 |
| 4,695,829 | A | * | 9/1987  | Everett et al. ............... 337/333 |
| 4,837,483 | A | * | 6/1989  | Kling ......................... 252/181.6 |
| 5,206,622 | A | * | 4/1993  | Lattari ......................... 337/365 |
| 5,808,539 | A | * | 9/1998  | White .......................... 337/102 |
| 6,133,817 | A | * | 10/2000 | Hofsass et al. .............. 337/100 |

FOREIGN PATENT DOCUMENTS

| EP | 43406 A1   | * | 1/1982  | .......... H01H/73/28 |
| JP | 1-279532 A | * | 11/1989 | .......... H01H/37/54 |
| JP | 2001-6514 A | * | 1/2002  | .......... H01H/73/22 |

* cited by examiner

Primary Examiner—Anatoly Vortman
(74) Attorney, Agent, or Firm—Russell E. Baumann; Frederick J. Telecky, Jr.

(57) ABSTRACT

A creep acting thermostatic switch (30) has an oblong, electrically conductive cup-shaped housing (32) formed with a side wall (32b) extending upwardly from a bottom wall (32a). A generally J-shaped creep acting thermostatic member (38) has a short leg (38a) attached to the side wall, a long leg (38b) extending across the cavity formed in the housing and a bight portion between the legs having a flattened surface portion (38c) to prevent interference with the corner between the side wall and bottom wall. A movable electrical contact (40) is mounted on the free end of the long leg and is movable into and out of engagement with a stationary electrical contact (37) mounted on a lid (36) received on the side wall. This arrangement allows for a thermostatic member having an optimized length to width ratio to provide maximum disc forces for a given housing size.

8 Claims, 2 Drawing Sheets

CREEP ACTING MINIATURE THERMOSTATIC ELECTRICAL SWITCH AND THERMOSTATIC MEMBER USED THEREWITH

FIELD OF THE INVENTION

This invention relates generally to thermostatic electrical switches and more particularly to such switches having a creep acting thermostatic member.

BACKGROUND OF THE INVENTION

Thermostatic electrical switches using a heat responsive thermostatic switching element comprising an element formed of metal layers having different coefficients of thermal expansion, such as a bimetal element, are either snap-acting or creep acting. In snap-acting switches the thermostatic element is formed into a dished configuration which will change from one dished configuration, e.g., concave, to an opposite dished configuration, e.g., convex, upon selected changes in temperature. An example of this type of switch is shown in U.S. Pat. No. 3,430,177. Switches of this type, comprising a cantilever mounted snap-acting member having a movable contact attached to its free distal end and movable into and out of engagement with a stationary contact, are used to protect motors, generators, transformers and other electrical apparatus from overheating caused by excessive currents or other temperature conditions. In order to closely monitor the temperature of the apparatus, the switches are placed within the apparatus and are therefore miniaturized in order to be used with miniaturized motors, generators, transformers and the like. Switches of the type shown in the above noted patent are widely used with many millions of such switches in use.

In creep acting switches, the thermostatic element is formed into a generally flat plate which bends as its temperature changes. A general guideline in the design of cantilever mounted creep thermostatic elements is that a 2:1 length to width ratio is required for good, predictable creep action of the thermostatic element. Creep action thermostatic elements made according to the guideline generally require a larger housing than is required for the snap-acting elements described above. Creep acting switches are used, in small appliances, such as heating pads, to maintain a generally constant temperature.

SUMMARY OF THE INVENTION

It is an object of the present invention to provide a creep acting thermostatic element made in accordance with the recommended length to width ratio and at the same time be sized so that it can be used in a package size comparable to that used for snap-acting thermostatic members. Another object of the invention is the provision of a miniaturized thermostatic switch having a creep acting, cantilever mounted thermostatic switch having a creep acting, cantilever mounted thermostatic element which can be mounted in a miniaturized housing generally just large enough for snap-acting members. Yet another object is the provision of a creep type thermostatic switch and switching element which is free of the prior art limitations noted above.

Briefly, in accordance with the invention, a creep acting thermostatic element comprises a generally flat blade of suitable thermostatic material such as bimetal which has been permanently deformed into a generally J-shaped configuration. This arrangement allows for an effective length almost the same length as the housing. The J-configuration provides a means for using a wider blade in a smaller package thereby increasing disc forces for a given size package which in turn increases cycle life. According to a feature of the invention, a relatively flat portion of the blade is formed between the two legs and is used to avoid interference with the corner formed between the end wall and the bottom wall of the housing.

Other objects and features of the invention will become more readily understood from the following detailed description and appended claims, when read in conjunction with the accompanying drawings in which like reference characteristic's designate like parts throughout the FIGURES thereof.

BRIEF DESCRIPTION OF THE PREFERRED EMBODIMENTS

Figure 1:
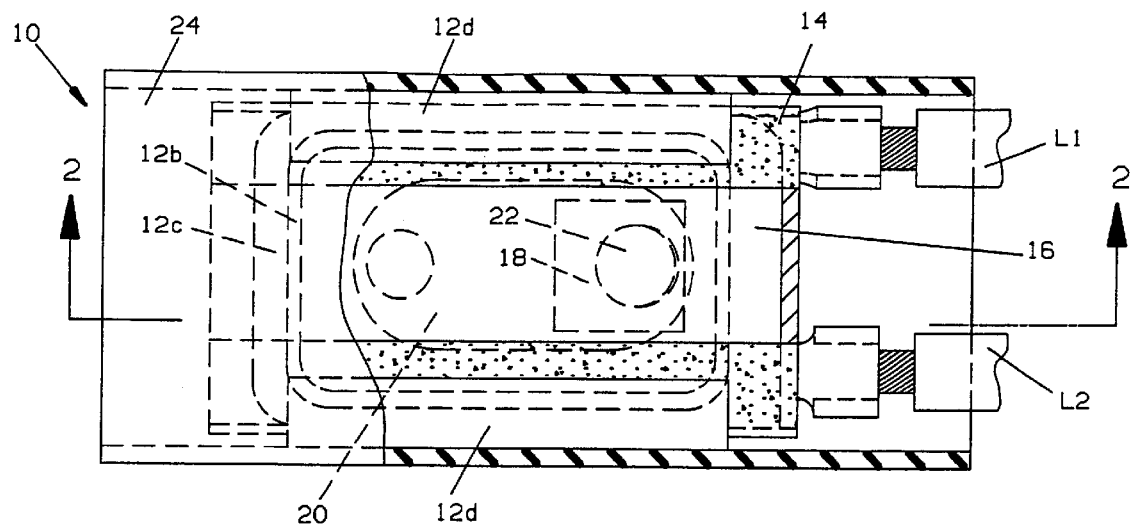
FIG. 1 is a top plan view of a prior art miniature thermostatic switch comprising a snap-acting thermostatic disc element shown in dashed lines.
Figure 2:
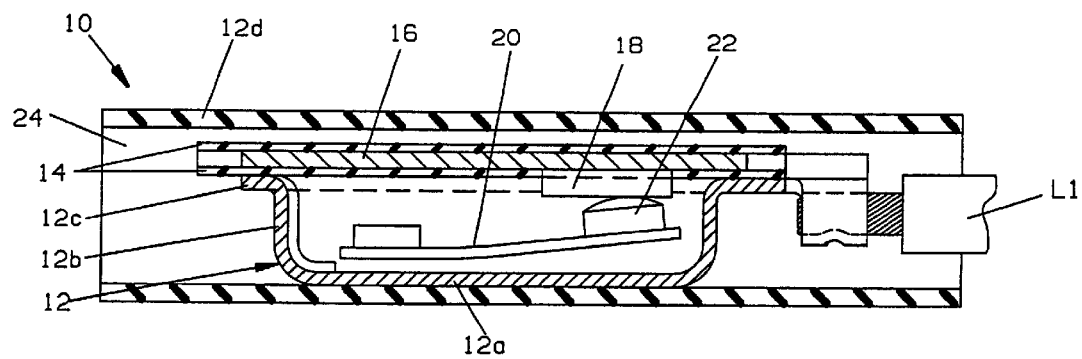
FIG. 2 is a cross sectional view taken on line 2—2 of FIG. 1.

With reference to FIGS. 1–2, a prior art miniature thermostatic switch 10 is shown comprising a metallic housing member 12 in the form of an oblong cup-shaped can having a bottom wall 12a and upstanding side walls 12b forming an oblong switch chamber having a generally rectangular elevational cross section. A ledge is formed around the periphery of the switch chamber by outwardly extending flange portions 12c formed at the distal free end of wall 12b. An electrically insulative gasket 14 is placed on flange portion 12c with a lid 16 disposed on top of the gasket and clamped thereto by bent over portions 12d of flange portion 12c. Gasket 14 is provided with a window and a stationary electrical contact 18 is attached to lid 16 and projects through the window.

A snap-acting thermostatic disc member 20 such as a dished bimetallic member, has one opposite end attached to bottom wall 12a of housing member 12 and is provided with a movable electrical contact 22 at its opposite free end adapted to move into and out of engagement with stationary contact 18 upon movement of disc member 20 from one dished configuration to its opposite dished configuration. Suitable terminal leads L1, L2 are respectively attached to the housing and lid. The device is shown inserted into an electrically insulative heat shrinkable sleeve 24 to provide electrical isolation from its environment. Further details of the snap-acting switch are shown and described in U.S. Pat. No. 3,430,177, the disclosure of which is included herein by this reference. As described, the degree of miniaturization is essentially limited to the space required for a snap-acting disc member which will provide sufficient snap movement between open and closed contact positions for a given range of electrical current.

Figure 3:
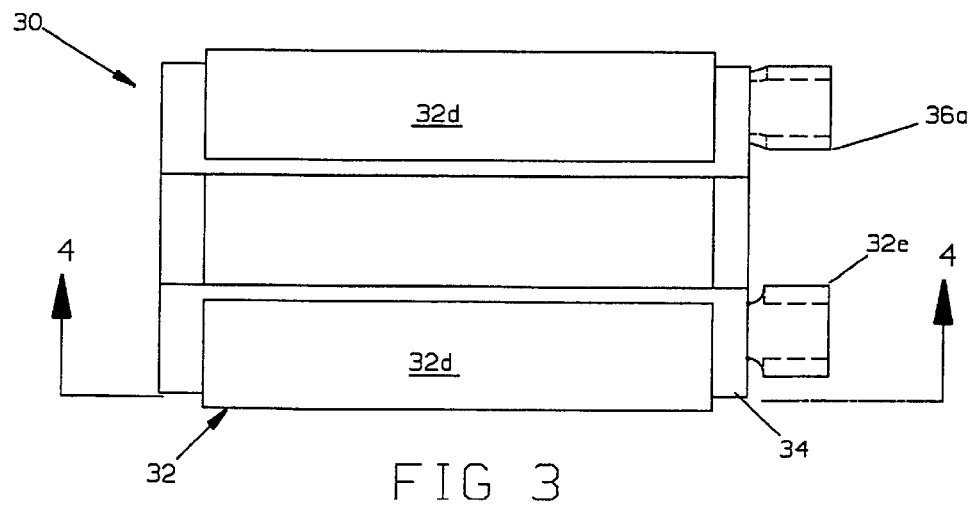
FIG. 3 is a slightly smaller scale top plan view of a miniature thermostatic switch made in accordance with the invention comprising a creep acting thermostatic blade.
Figure 4:
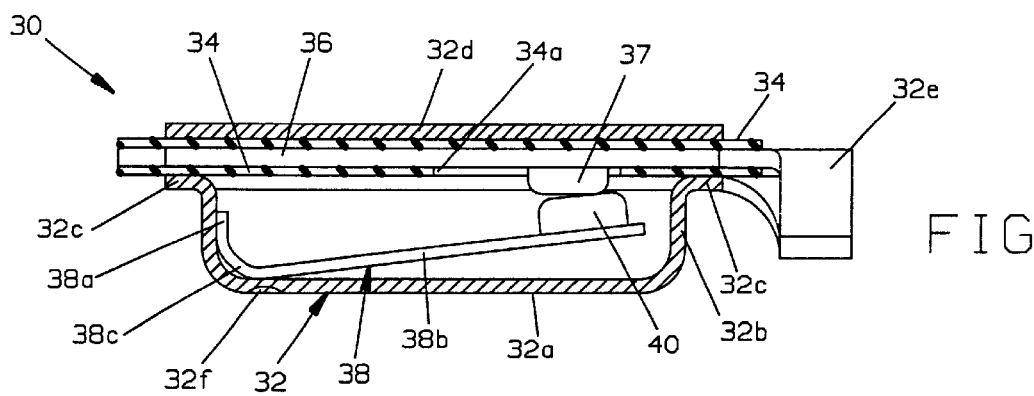
FIG. 4 is an enlarged cross sectional view taking on line 4—4 of FIG. 3.
Figure 5:
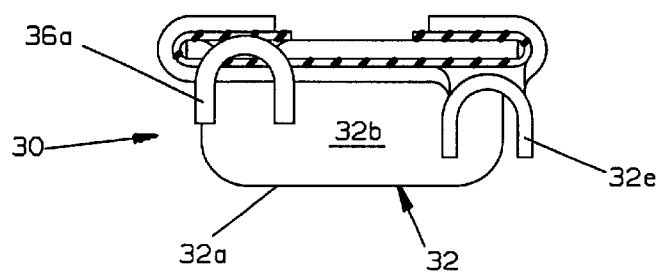
FIG. 5 is a side elevational view of the FIG. 3 switch using the FIG. 3 scale.

As noted above, a general guideline in the design of cantilever-style creep acting thermostatic blade is that a 2:1 length to width ratio is required for good, predictable creep action of the blade. FIGS. 3–5 relate to a switch housing having a creep acting thermostatic blade with a length to width ratio which satisfies the design guideline which can be mounted in a housing whose overall package size is comparable, for example, to the size commonly used for miniaturized snap-acting switches.

Creep acting thermostatic electrical switch 30 made in accordance with the invention comprises an oblong cup-shaped housing 32 formed of suitable electrically conductive metal having a bottom wall 32a with a side wall 32b extending around the outer periphery of bottom wall 32a enclosing a switch chamber generally shaped as a parallelepiped. A ledge is formed around housing 32 by outwardly extending flange portions 32c of side wall 32b on which is disposed a sheet 34 of suitable electrically insulative gasket material. A generally flat lid 36 of electrically conductive material is disposed on top of sheet 34 on the ledge and securely fastened thereto by deforming extended flange portions 32d on two opposite sides of the housing over the sides and onto the top of the lid with sheet 34 interposed therebetween. Sheet 34 is formed with a window 34a aligned with a stationary electrical contact 37 mounted, as by welding, to the lower surface of lid 36.

Creep acting thermostatic member 38, formed of suitable generally flat material such as a bimetal, is deformed into a generally J-shaped configuration having a short leg 38a which is attached to side wall 32b of housing 32, as by welding, and a long leg 38b which extends across the switch chamber to a location adjacent to but spaced from side wall 32b on the opposite side of the housing. A movable electrical contact 40 is mounted on the top side of leg 32b adjacent to its free distal end and is adapted to move into and out of electrical engagement with stationary contact 37. Preferably, a generally flat portion 38c is formed in the bight portion between legs 38a, 38b which serves to space the blade from the corner portion of housing 32 between side wall 32b and bottom wall 32a and thus avoid any interference with operation of the bimetal blade. The active or movable portion of blade 38 essentially is the length of leg 38b. Respective terminals 32e, 36a extend from housing 32 and lid 36 for attachment to electrical leads (not shown). The switch is calibrated by taking an open switch, bringing it to the selected temperature and deforming housing 32 at 32f to thereby bias thermostatic member 38 upwardly, as seen in FIG. 4, until the contacts close.

Figure 6:
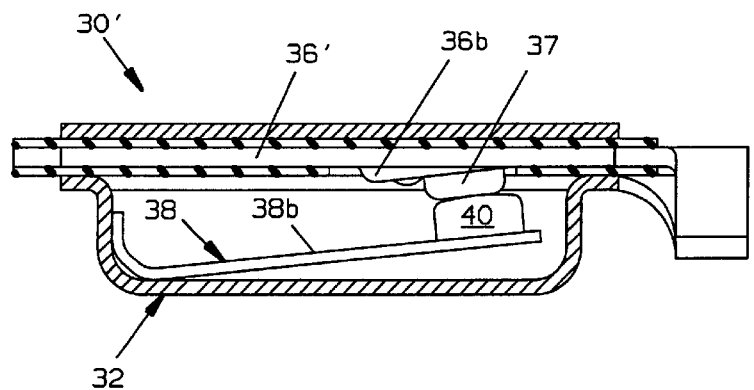
FIGS. 6 and 7 are similar to FIG. 4 showing alternate embodiments of the invention.
Figure 7:
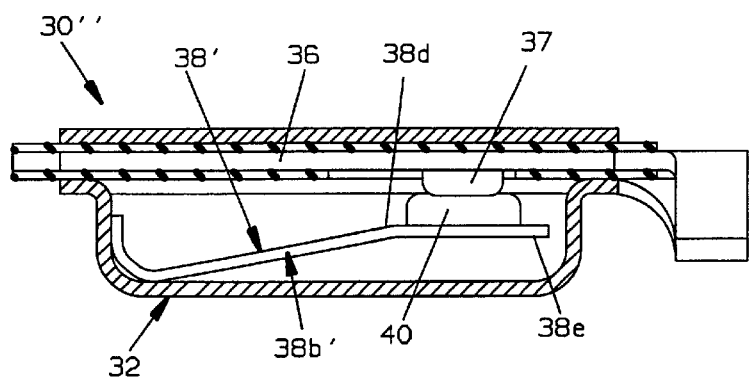

By configuring the creep blade in a generally J-shape, a wider blade can be employed in a given package thereby resulting in higher blade forces which in turn increases cycle life through an enhanced ability to break tack welds. By way of example, switches made in accordance with the invention had a thermostatic blade with a thickness of 0.012, a width 0.150 and a length 0.413 inches, FIGS. 6 and 7 show alternate embodiments in which the stationary and movable electrical contacts are mounted in the switch with improved alignment relative to one another in the closed or contacts engaged position. In switch 30', FIG. 6, lid 36' is deformed at 36b so that the portion of the lid on which stationary contact 37 is mounted is skewed forming a selected acute angle with the remainder of the lid so that the stationary electrical contact mounting portion lies in a plane generally parallel to a plane in which long leg 38b of thermostatic member 38 lies, including the free distal end thereof mounting movable electrical contact 40, at a time when the contacts engage one another.

In switch 30", FIG. 7, long leg 38b' of thermostatic member 38' is permanently deformed at 38d so that the distal end portion 38e of member 38 which mounts movable electrical contact 40 lies in a plane generally parallel to the mounting portion of stationary electrical contact 37 on lid 36 at a time when the contacts engage one another.

Although the present invention has been illustrated and described in terms of a specific preferred embodiment, it will be apparent that changes and modification are possible without departing from the spirit and scope of the invention as defined in the appended claims.

What is claimed:

1. A thermostatic switch comprising an electrically conductive can having a bottom wall and an upstanding side wall forming an open ended, generally parallelepiped shaped cavity therein, a creep acting thermostatic member having a generally J-shaped configuration formed with a short leg fixedly attached to the side wall and a long leg extending across the cavity, the long leg having a free distal end, a movable electrical contact mounted on the long leg adjacent to the free distal end thereof, a lid received on the upstanding wall closing the cavity, a stationary electrical contact mounted on the lid electrically isolated from the can, first and second terminals electrically connected to the can and the stationary electrical contact respectively, the movable electrical contact being movable into and out of electrical engagement with the stationary electrical contact.

2. A thermostatic switch according to claim 1 in which the lid is formed of electrically conductive material and further comprising an electrically insulative gasket interposed between the can and the lid to provide electrical isolation therebetween.

3. A thermostatic switch according to claim 1 in which a bight portion is formed between the short and long legs and the bight portion is disposed adjacent the bottom wall of the can.

4. A thermostatic switch according to claim 3 in which the bight portion includes a generally flat surface portion to prevent interference between a corner formed by the side wall and the bottom wall and the thermostatic member.

5. A thermostatic switch according to claim 1 in which the long leg generally lies in a plane which forms a selected acute angle with a plane in which the lid lies when the movable electrical contact is in electrical engagement with the stationary electrical contact and the stationary and movable electrical contacts are mounted on surfaces which lie in planes generally parallel to one another when the contacts move into electrical engagement.

6. A thermostatic switch according to claim 5 in which the portion of the lid mounting the stationary contact is deformed so that it lies generally in a plane which forms the selected acute angle with the remainder of the lid.

7. A thermostatic switch according to claim 5 in which the free distal end of the long leg of the creep acting thermostatic member is deformed so that the free distal end on which the stationary contact is mounted lies in a plane generally parallel to the lid when the contacts move into electrical engagement.

8. A creep acting thermostatic member formed of a generally single piece flat blade of thermostatic metal deformed into a generally J-shaped configuration having a short leg for attachment to a support and a long leg having a distal free end, a movable electrical contact mounted on the long leg adjacent to the distal free end and a bight portion formed between the short and long legs having a generally flat surface portion.

* * * * *